United States Patent [19]

Ferrari et al.

[11] 4,233,290
[45] Nov. 11, 1980

[54] METHOD OF TREATING DOMESTIC ANIMALS

[75] Inventors: Lorenzo Ferrari; Ernani Dell'Acqua; Giorgio Quaglia, all of Milan, Italy

[73] Assignee: SPA-Societa Prodotti Antibiotici, S.p.A., Milan, Italy

[21] Appl. No.: 16,616

[22] Filed: Mar. 1, 1979

[51] Int. Cl.$^3$ .......................... A61K 37/48; A23C 9/12
[52] U.S. Cl. ......................................... 424/94; 426/61; 426/63
[58] Field of Search ....................... 424/94; 426/61, 63

[56] References Cited

U.S. PATENT DOCUMENTS

| | | | |
|---|---|---|---|
| 3,338,719 | 8/1967 | Sawada et al. | 426/61 |
| 3,859,435 | 1/1975 | Bruzzese et al. | 424/94 |
| 3,937,815 | 2/1976 | Bruzzese et al. | 424/94 |

OTHER PUBLICATIONS

Brisou et al.-Chem. Abst., vol. 83, (1975), p. 188,807j.
D. B. Guralnik, "Webster's New World Dictonary," Second College Edition.

*Primary Examiner*—Delbert R. Phillips
*Attorney, Agent, or Firm*—Wenderoth, Lind & Ponack

[57] ABSTRACT

The present invention provides a method of treating domestic animals which are infected or endangered by micro-organisms, as well as solid and liquid nutriments for domestic animals comprising lysozyme and/or at least one non-toxic salt thereof.

The present invention also provides, as new compounds, lysozyme phosphate, glycerophosphate, lactate, gluconate and hexametaphosphate, as well as a process for the preparation thereof.

10 Claims, No Drawings

METHOD OF TREATING DOMESTIC ANIMALS

BACKGROUND OF THE INVENTION

Lysozyme, a protein discovered by Fleming in 1922, is found in all living organisms (plants, animals, bacteria, algae, fungi, etc.). Its activity occurs at the membrane level of numerous bacteria, in particular those which are gram-positive. In higher animals, it represents a natural immunity factor in the defence against infection. Apart from its own lytic activity, lysozyme is able to potentiate the action of numerous antibiotics, micro-organisms partially lysed by lysozyme becoming more sensitive to antibiotics.

Another characteristic of lysozyme is its beneficial influence on the digestive processes in mammals which is manifested by prompt normalisation of the intestinal flora, with consequent saving or improvement of the nitrogen metabolism.

Although found in both the animal and plant kingdoms, lysozyme is currently produced on an industrial scale exclusively by extracting from egg white.

We have recently carried out test studies with lysozyme in chickens to combat some of the diseases more frequently seen and to observe any effect on growth.

As is known, chickens are usually vaccinated by aerosols three times in their lives in order to prevent pathological developments. However, 48 hours after vaccination, symptoms of stress appear and the birds fall into a state of prostration with loss of appetite and, consequently, interruption of growth. In order to prevent this debility, antibiotic treatment is given to the birds 36 hours after vaccination. In most cases, this treatment gives positive results. However, as is known, antibiotics can cause the development of resistant strains and when this treatment is used in combating certain forms of respiratory diseases, the results obtained are ineffective because of the resistant bacterial forms present in the diseased chickens.

As a result of our trials, we have found that, in combating vaccination stress with lysozyme, there were two advantages:

(1) the antibiotic dose could be lowered and
(2) the antibiotics could frequently be eliminated altogether so that they need only be used to combat bronchopulmonary diseases when such diseases appear.

SUMMARY OF THE INVENTION

The invention provides a method of treating domestic animals endangered by or suffering from infections of micro-organisms, wherein lysozyme or a non-toxic salt of lysozyme is administered to a domestic animal.

DETAILED DESCRIPTION OF THE INVENTION

Lysozyme can be easily administered, for example in drinking water. In this way, continual administration throughout the day is assured; if preferred, the lysozyme can also be mixed with a vaccine or given with the feed. Treatment usually lasts 3 to 4 days following vaccination.

Chickens are prone to diseases of the respiratory organs. This phenomenon is usually seen in autumn and winter, i.e. periods in which the change of air in the sheds is less frequent because of the difference in internal and external temperature. Antibiotic treatment is normally also used here to overcome these manifestations which, practically speaking, include malaise with loss of appetite, resulting in delayed growth. Treatment with lysozyme has resolved many of these cases where prolonged antibiotic treatment has proved to be of no avail. Very often, antibiograms are used to choose a more appropriate antibiotic but a substance found to be effective in vitro is not always effective in vivo.

During our trials, 4 groups of about 11,000 chickens each (average age 45 days) caught a respiratory-type illness which did not resolve even after 10 days of antibiotic treatment.

Therefore, lysozyme dissolved in drinking water was administered at a dosage of 15 mg/kg/day to 3 groups. About 24 hours later, the chickens began to recover and to eat regularly, whilst those which had not been treated continued to deteriorate and had to be killed.

This therapy with lysozyme was continued for another 15 to 20 days, after which the chickens were killed. When the mean weights of the treated chickens were controlled, we found that not only had they made up in weight the 10 days with little or no food but that they had also reached a final mean weight of about 10% more than the normal weight. This was confirmed in another trial in which lysozyme was used to combat vaccination stress.

The chickens were treated three times (at the age of 2, 18 and 35 days) for 5 days each, corresponding to 3 vaccinations. At the end of the experiment, the 11,000 chickens treated with lysozyme had increased in weight 6% more than the untreated chickens.

Because of these observations, specific trials were carried out to verify the auxetic effect of lysozyme and gave very satisfactory results.

In view of this, we were prompted to verify the auxetic action of lysozyme in combination with other substances already well known per se endowed with this activity, for the purpose of verifying a possible synergistic action.

These trials proved, as a whole, to be positive, thereby demonstrating their validity.

Another consideration was made when observing that very often alimentary supplements can contain antibiotics which, on the one hand, act as auxetics and, on the other hand, as immunodepressants, as is often seen in poultry farms of the intensive type, where a commonplace infection can, at times, have disastrous consequences, resulting in a high incidence of fowl plague. Even more so in this case does the use of a combination with lysozyme seem evident, endowed not only with an auxetic but also a proimmunation action.

In conclusion, we thought it useful to use lysozyme at doses varying from 1 to 50 mg/kg/day and preferably from 2 to 15 mg/kg/day, in conjunction with conventional diet and zootechnical supplements, taking into account both the above-mentioned activities which the enzyme possesses.

We found that excellent results can be obtained both by daily administration and by giving lysozyme during the final days of housing. As mentioned above, a further aspect of the present invention is that particular lysozyme salts are of very practical use in the above-mentioned cases. Lysozyme salts are readily soluble in water and, therefore, can be administered in drinking water. Thus, lysozyme need not necessarily be combined with the feed. In other cases, lysozyme salts which are only slightly soluble in water were obtained and, in such cases, are advantageously mixed in a solid state with the feeds.

Of the salts tested, both soluble and insoluble in water, some are known from the literature, whilst others are new salts.

The soluble salts can be prepared by salifying lysozyme base with an appropriate free acid, whereas the insoluble salts can be made by double exchange between a soluble lysozyme salt, such as the hydrochloride, and a soluble salt of the anion required, such as a sodium salt.

The new lysozyme salts prepared include lysozyme phosphate, glycerophosphate, lactate, gluconate and hexametaphosphate.

The following describes various tests which have been carried out using lysozyme and lysozyme salts:

Vaccination Stress in Poultry 3 groups of about 10,000 chickens each were vaccinated by aerosol. 36 hours after vaccination, antibiotics were given to a first group and half the amount of the same antibiotic dose, together with lysozyme at a dosage of 5 mg/kg/day, was given to a second group, treatment lasting 5 days in both cases.

The third group only received lysozyme at a dosage of 15 mg/kg/day, dissolved in water, starting from the same day as the vaccination and lasting for another 4 days.

Blood samples were taken from 20 chickens from each group for the microbiological determination of the amount of lysozyme before vaccination, 24 hours after vaccination and towards the end of the treatment with antibiotics + lysozyme or lysozyme alone.

The following Table gives the average lysozyme content in the 3 groups during the above-mentioned periods:

| Lysozyme blood levels in vaccinated chickens under antistress treatment | | | | | | | | |
|---|---|---|---|---|---|---|---|---|
| only antibiotics | | | Half the antibiotic dose + 5 mg/kg/day lysozyme | | | 15 mg/kg/day lysozyme | | |
| before vaccin. | after vaccin. | end of treatment | before vaccin. | after vaccin. | end of treatment | before vaccin. | after vaccin. | end of treatment |
| 1.87 | 2.34 | 2.05 | 1.91 | 2.27 | 1.98 | 1.95 | 2.4 | 3.27 |

From the above Table, it can be seen that, following vaccination, the chickens tend to increase their own lysozyme content and, after antibiotics, this amount drops towards the initial values seen before vaccination. On the other hand, lysozyme at a dosage of 15 mg/kg/day increases the lysozyme content considerably.

Generally speaking, no differences were seen among the 3 groups. In conclusion, therefore, lysozyme can replace antibiotics in combating vaccination stress.

Bronchpulmonary Diseases in Poultry 4 groups of 11,000 chickens each (40 days old) were affected with a serious respiratory disorder. The 4 groups had been regularly vaccinated three times and each time had been given antibiotics to combat vaccination stress.

When bronchopulmonary disease broke out, they were treated with antibiotics but after 10 days there was no sign of recovery: on the contrary, they continued to deteriorate and hardly ate anything. Three groups were then given lysozyme dissolved in water at a dosage of 15 mg/kg/day. They recovered almost immediately, whilst the non-treated group had to be killed since they were in a continuous state of prostration. They weighed 1.6–1.7 kg. and were 55 days old.

The lysozyme treatment was continued in the three groups, still at the same dose, for another 15 days, i.e. until they were 65 days old. They were then slaughtered and their mean weight was 2.510 kg.

Lysozyme as a Growth Factor in Poultry

In order to verify the auxetic activity of lysozyme, we experimented on 4 groups of 10,000 chickens each. The first group was given a normal diet and the second group the same diet but with lysozyme at a dosage of 2 mg/kg/day, added to their drinking water, throughout their life period.

The third group was given feed and water for the first 50 days. During the final 15 days of life, lysozyme at a dosage of 15 mg/kg/day was dissolved in their drinking water and the same feed given.

The fourth group was treated in the same way except that the lysozyme (still at the same dosage) was mixed with the feed.

When they were 66 days old, the 4 groups were slaughtered and their weights were controlled.

The mean weights were:
1st group: 2.314 kg.
2nd group: 2.541 kg.
3rd group: 2.639 kg.
4th group: 2.607 kg.

Studies in Mammals

We carried out experimental studies to investigate nitrogen metabolism saving action or increase by lysozyme when added to the diet of domestic animals (rabbits, pigs, dogs, cattle, sheep, goats, etc.).

One of the studies involved 20-day old piglets fed with reconstituted cow's milk. We chose this animal species because its intestinal flora is very similar to that of other mammals and because of its easy management in a metabolic study.

The study was carried out on 2 groups: the first was composed of 3 piglets and the second of the same number from the same litter. The small number of animals used in each experiment was due to the fact that it was essential that they came from the same litter. The piglets, weaned after 20 days, were placed in metabolic cages and fed with partially skimmed, powdered cow's milk, appropriately reconstituted.

The milk had the following composition:
N = 336 mg per 100 g.
Ca = 108 mg per 100 g.
P = 90 mg per 100 g.

Calorie intake was rigorously kept in proportion to the body weight throughout the experiment, whilst lysozyme (or its salts) was administered at the dosage of 100 mg/100 g. of reconstituted cow's milk.

Six 3-day periods of metabolic balance were calculated, plus an initial one before treatment with lysozyme (period 0) for all the pigs.

The Kjeldhal method was used to determine the amount of nitrogen in the faeces at the end of each period.

The results obtained are given in the following Table:
N balance (mg/kg/day)

| Period | 0 | I | II | III | IV | V | VI |
|---|---|---|---|---|---|---|---|
| Controls not treated (3 pigs) | 368.2 | 366.6 | 526.5 | 576.4 | 499.8 | 574.9 | 656.8 |
| Treated (3 pigs) | 364.6 | 462.8 | 466.1 | 579.5 | 586.0 | 577.5 | 655.2 |
| Percentage of N administered per os and excreted in the faeces | | | | | | | |
| Controls not treated (3 pigs) | 4.8 | 4.8 | 3.9 | 4.0 | 6.1 | 5.7 | 5.3 |
| Treated (3 pigs) | 4.9 | 3.5 | 3.4 | 3.0 | 5.4 | 5.4 | 4.5 |

From the data it can be deduced that the percentage of nitrogenous substances absorbed by the gastro-intestinal tract of piglets fed with cow's milk significantly increased following treatment with lysozyme (or its salts) added to a young mammal's normal diet.

This is indicated by the lower values of nitrogen which were ingested and excreted in the faeces; the results seen in piglets were also seen in other mammals, following the breast feeding period, when lysozyme (or its salts) was added at the dosage of 10 mg/100 mg of feed.

The following Examples are given solely as illustrations and are not limiting, since lysozyme, whether in its basic form or as a salt with an organic or inorganic acid, was seen to be particularly useful as an additive in any diet or zootechnic adjuvant containing antibiotics (tetracycline, bacitracin, zincobacitracin, aminoxydine sulphate, etc.), oligoelements, vitamins, aminoacids, mineralisers, etc.

EXAMPLE 1

100 g. of traditional feed based on cornflour, alfalfa flour, soybean flour, fossil meal, contains:

| | |
|---|---|
| lysozyme citrate | 10 mg. |
| thiamine | 0.5 mg. |
| riboflavin | 0.6 mg. |
| niacin | 8 mg. |
| calcium pantothenate | 2 mg. |
| pyridoxal phosphate | 0.6 mg. |
| inositol | 100 mg. |
| choline chloride | 150 mg. |
| biotin | 0.3 mg. |
| folic acid | 0.5 mg. |
| menadione | 0.5 mg. |
| α-tocopherol | 0.5 mg. |

EXAMPLE 2

To a mixture of 120 g. of cornflour and 70 g. of soya flour, add:

| | |
|---|---|
| lysozyme hexametaphosphate | 15 mg. |
| bonemeal | 7 g. |
| iodine salts | 2 g. |
| vitamin A | 400 mg. |
| vitamin $D_3$ | 400 mg. |
| manganese sulphate | 60 mg. |

EXAMPLE 3

To a meal mixture made up of 50 g. of cornflour, 5 g. of wheat meal, 3 g. of alfalfa flour, 30 g. of soybean flour, add:

| | |
|---|---|
| lysozyme | 3 mg. |
| calcium carbonate | 1.5 g. |
| bonemeal | 3 g. | whole mycelium containing chlorotetracycline 2.5% on the total weight.

EXAMPLE 4

To a standard diet, having the following composition percent: cornflour 78.5; soya flour 15.5; bonemeal 2.5 and calcium carbonate 0.5, add:

| | |
|---|---|
| oligoelement salts | 2% |
| riboflavin, calcium pantothenate, choline chloride, niacin, vitamin $D_3$ | 1% |
| lysozyme phosphate | 0.01% |

EXAMPLE 5

To a normal integrated feed, add 250–350 g/quintal of a biological material containing natural live cells of Saccharomyces and Kluyveromyces. This additive has the following composition percent:

| | |
|---|---|
| lysozyme lactate | 0.02 |
| cultures containing 6,000,000/g. of live cells | 0.20 |
| proteins | 18.75 |
| fats | 3.86 |
| raw fibre (roughage) | 7.88 |
| non-nitrogenous extractives | 52.98 |
| organic substances | 6.93 |
| water | 9.60 |

The colonisation of live cells and the lysozyme determine fermentation of the alimentary mass, with consequent increase in absorption of the nutritive elements and microbial antagonisation as regards pathogenic micro-organisms.

EXAMPLE 6

| | |
|---|---|
| lysozyme hexametaphosphate | 0.02 % |
| dried yeast | 10 % |
| cornflour | 60 % |
| barley flour | 4 % |
| soya flour | 10 % |
| alfalfa flour | 5 % |
| animal fats | 0.5 % |
| calcium carbonate | 4.35 % |
| bonemeal | 3 % |
| bicalcium phosphate | 1.75 % |
| sodium chloride | 0.35 % |
| methionine | 0.05 % |
| Premix | 1 % |

Premix has the following composition per kg. of finished product:
vit.A 10,000 I.U.; vit.$D_3$ 2,000 I.U.; vit.E 20 mg.; vit.K 2 mg.; vit.$B_1$ 1 mg.; vit.$B_2$ 5 mg.; vit.$B_6$ 1 mg.; vit.$B_{12}$ 0.01 mg.; nicotinic acid 25 mg.; pantothenic acid 5 mg.; folic acid 1 mg.; choline 250 mg.; Fe 20 mg.; Co 2 mg.; Mn 200 mg.; Cu 15 mg.; I 2 mg.; Se 0.2 mg.; Mo 0.1 mg.; BTH 100 mg.

EXAMPLE 7

To a standard rabbit diet having the following composition per 100 g.:

| | |
|---|---|
| soya flour | 11 g. |
| sunflower flour | 4 g. |
| beef meal | 3 g. |
| skim dried milk | 4 g. |
| cornflour | 30 g. |
| barley flour | 15 g. |
| alfalfa flour | 10 g. |
| wheatmeal | 15 g. |
| glutinated cornflour | 5 g. |
| calcium carbonate | 1 g. |
| bihydrate bicalcium phosphate | 1 g. |
| sodium chloride | 0.5 g. |
| multi-vitamin and oligomineral complex | 0.5 g. (1) | add 10 mg. of lysozyme lactate (preferably mixed with the 4 g. of skim dried milk). (1) See Example 6 for the composition of this complex.

EXAMPLE 8

To a standard cattle diet, composed of dried hay and water ad libitum, add, at a level varying between 10 and 30 ppm, an auxetic composition having the following composition percent:

| | | |
|---|---|---|
| cornflour | 66.7 | |
| wheatmeal | 15.8 | |
| soya flour | 6.7 | |
| dehydrated alfalfa flour | 5 | |
| minerals | 5 | |
| oligoelements and vitamin complex | 0.8 | (see Example 6 for composition) |

Add lysozyme at a dosage of 20 mg/kg aminal/day.

The following Examples describe the preparation of the new salts of lysozyme.

EXAMPLE 9

4.76 g. lysozyme are suspended in 50 ml. water. 237 mg. Phosphoric acid, dissolved in 20 ml. water, are added, while stirring, the pH thereby decreasing to 3.40. An opalescent solution is obtained which is then filtered through diatomaceous earth. The limpid solution obtained, which contains lysozyme phosphate, is lyophilised or precipitated with a solvent. Lysozyme phosphate is a white, microcrystalline powder with the following characteristics:
pH (1% solution in water)=3.45
Lysozyme content: 91.5% in the anhydrous salt.
Phosphorus: 2.57% by weight, equal to 8.1% by weight of phosphoric acid, referred to the anhydrous salt.

EXAMPLE 10

261 mg. lactic acid, dissolved in 10 ml. water are added, while stirring, to a suspension of 4.98 g. lysozyme base in 50 ml. water. As the acid is added, the lysozyme base tends to dissolve and the pH decreases. After all the acid has been added, a slightly cloudy solution is obtained which is filtered and lyophilised.

The lysozyme lactate obtained is a white powder with the following characteristics:
pH (1% solution in water): 4.40
lysozyme content: 88.7% in the anhydrous salt.

EXAMPLE 11

256 mg. sodium hexametaphosphate, dissolved in 10 ml. water, are added, while stirring, to a solution of 5 g. lysozyme hydrochloride in 60 ml. water. A white precipitate is obtained which is filtered off, washed with iced water and dried in a vacuum. Lysozyme hexametaphosphate is obtained in the form of a white powder which is insoluble in water and has the following characteristics:
pH (1% suspension in water): 3.70
lysozyme: 90.3% in the anhydrous salt.
phosphorus: 3.42% by weight in the anhydrous salt, equal to 8.82% by weight as hexametaphosphoric acid.

We claim:

1. A method of treating domestic animals endangered by or suffering from vaccination stress, wherein a member selected from the group consisting of lysozyme and non-toxic salts of lysozyme is administered to a domestic animal endangered by or suffering from vaccination stress in amounts effective to counteract the effects of such vaccination stress.

2. Nutriments for domestic animals comprising a member selected from the group consisting of lysozyme and the non-toxic salts thereof in amounts effective to combat the effects of vaccination stress in said domestic animals.

3. A solid foodstuff for domestic animals comprising a member selected from the group consisting of lysozyme and non-toxic salts thereof in amounts effective to combat the effects of vaccination stress in said domestic animals.

4. A method according to claim 1 in which the lysozyme compound or the non-toxic salts thereof is administered in a dosage of 1 to 50 mg/kg/day.

5. A method according to claim 4 wherein the dosage is 2–15 mg/kg/day.

6. A method according to claim 1 wherein the lysozyme compound or the non-toxic salts thereof are administered orally to the domestic animal.

7. A method according to claim 6 wherein the lysozyme compound or the non-toxic salts thereof are mixed with the animals food and then administered to the domestic animal.

8. A method according to claim 1 wherein the domestic animals are treated with a non-toxic salt of lysozyme selected from the group consisting of lysozyme phosphate, lysozyme glycerophosphate, lysozyme lactate, lysozyme gluconate and lysozyme hexametaphosphate.

9. A nutriment according to claim 2 which comprises a non-toxic salt of lysozyme selected from the group consisting of lysozyme phosphate, lysozyme glycerophosphate, lysozyme lactate, lysozyme gluconate and lysozyme hexametaphosphate.

10. A foodstuff according to claim 3 comprising a non-toxic salt of lysozyme selected from the group consisting of lysozyme phosphate, lysozyme glycerophosphate, lysozyme lactate, lysozyme gluconate and lysozyme hexametaphosphate.

* * * * *